United States Patent [19]

Garrett

[11] 4,014,354
[45] Mar. 29, 1977

[54] DENTAL FLOSSING TOOL
[76] Inventor: Terry N. Garrett, 2725 Dundee Court, Fort Collins, Colo. 80521
[22] Filed: Oct. 3, 1975
[21] Appl. No.: 619,443
[52] U.S. Cl. .................................................. 132/90
[51] Int. Cl.² ......................................... A61C 15/00
[58] Field of Search ......................... 132/90, 91, 92
[56] References Cited

UNITED STATES PATENTS

| 1,091,789 | 3/1914 | Andren | 132/91 |
| 2,444,638 | 7/1948 | Dobbins | 132/92 R |
| 3,421,524 | 1/1969 | Waters | 132/92 R |

Primary Examiner—G.E. McNeill
Attorney, Agent, or Firm—Stephen P. Fox

[57] ABSTRACT

Dental floss is tensioned between a pair of spaced-apart, L-shaped arms attached to a handle. The configuration of the arms permits effective flossing of target areas within the mouth with minimal visual obstruction and facial distortion. The handle may be attached to the arms for right- or left-handed use. An electrical actuator attached to the handle reciprocates the dental floss in the target area.

11 Claims, 7 Drawing Figures

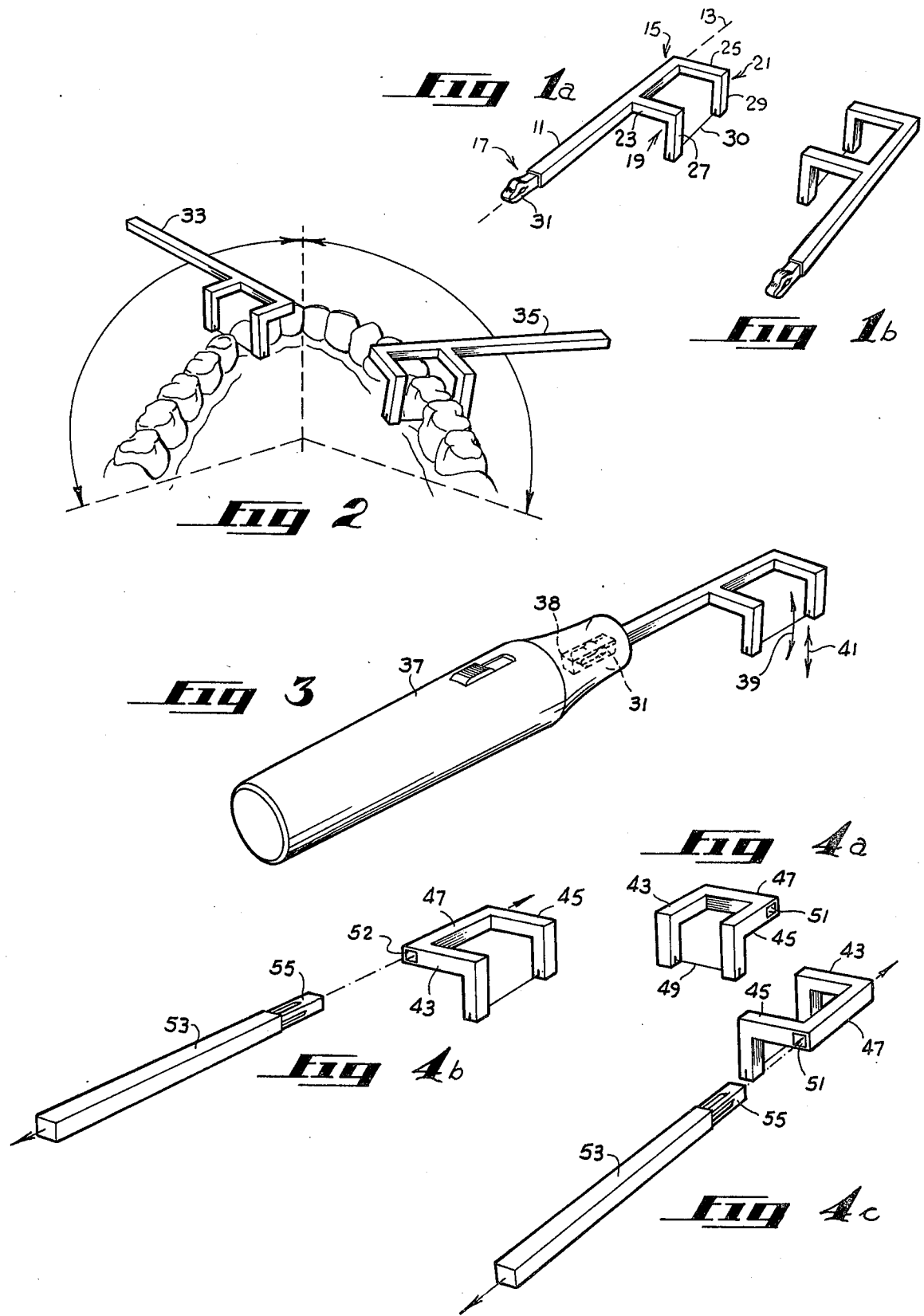

DENTAL FLOSSING TOOL

BACKGROUND OF THE INVENTION

The present invention relates generally to a tooth-cleaning device, and more particularly to a dental flossing tool.

The conventional manual dental flossing technique involves winding a length of dental floss around the first finger of each hand, drawing the floss taught between the fingers, and positioning one finger partially in the mouth and the other finger outside the mouth such that the floss can be gently guided between the teeth using the fingers and thumbs. The dental floss is held under tension against the surface of a tooth and guided slightly below the gum line. A vertical scraping motion is made on the side of each tooth to remove bacterial plaque and food particles lodged between the teeth and under the surface of the gums.

A variety of tools have been devised to assist in the dental flossing process. Typically, they embody means for suspending a short length of dental floss under tension. Heretoforeknown dental flossing tools are intended to aid the user in cleaning difficult-to-reach teeth. However, problems encountered in using such tools or using the conventional manual technique are that the face and lips must often be stretched or distorted significantly to gain access to the tooth target areas where flossing is desired. In addition, heretoforeknown flossing devices tend to obstruct or interfere with viewing of the flossing activity in the target area by the user. Furthermore, such tools tend to interfere with both the tongue and the cheek during flossing. Particularly difficult areas to floss are those between the second bicuspids and the molars in the upper and lower jaw. It is often difficult to apply and control the proper amount of force in the desired direction to achieve flossing activity which satisfactorily cleans the teeth without damaging gingival tissue.

SUMMARY OF THE INVENTION

The present invention provides a dental flossing tool which reduces facial distortion in use and increases the user's visibility of the flossing activity in the target area. The tool promotes ease of access to the target area while minimizing interaction between the flossing activity and the tongue or the cheek. The tool may be operated with a reciprocatory vertical motion similar to that used in brushing the teeth.

According to one illustrated embodiment of the invention, a pair of spaced-apart arms are disposed on one end of a handle. Each arm has a first portion extending laterally from the handle in a first direction and a second portion extending from the first portion in a second direction. A length of dental floss is tensioned between the ends of the second portions of the two arms, so that the floss is aligned parallel to the axis of the handle. Viewed cross-sectionally on a plane perpendicular to the axis of the handle, the two arms are L-shaped, and the dental floss is tensioned between the ends of the L's. The tool is configured in mirror-image versions for use in different areas of the mouth. The end of the handle includes means for securing the tool to a hand-held actuating mechanism which imparts reciprocatory motion to the dental floss tensioned between the two arms. The actuating mechanism may be the power unit of an electric toothbrush.

In another illustrated embodiment, the two L-shaped arms are disposed on an intermediate support member, the opposite ends of which are configured with receptacles for detachably securing a mating pin on the end of the handle. With this arrangement, the mirror-image versions of the tool are produced by simply inserting the handle in one or the other of the receptacles at opposite ends of the support member.

In use, flossing of the right half of the mandibular dentition and the left half of the maxillary dentition is achieved with one version of the tool; whereas flossing of the left half of the mandibular dentition and the right half of the maxillary dentition is achieved with the mirror-image version of the tool.

BRIEF DESCRIPTION OF THE DRAWINGS

FIGS. 1a and b are perspective views of mirror-image versions of the dental flossing tool of the present invention.

FIG. 2 is a perspective view of the teeth in one jaw illustrating the positioning of the dental flossing tool in use.

FIG. 3 is a perspective view of the dental flossing tool including an actuating mechanism for producing reciprocal motion of the dental floss.

FIGS. 4a, b and c are perspective views of an alternate embodiment of the dental flossing tool which may be assembled in either one of mirror-image versions.

DESCRIPTION OF THE PREFERRED EMBODIMENT

Referring now to FIG. 1a, there is one version of the dental flossing tool including a handle 11 having a longitudinal axis 13, a first end 15, and a second end 17. At the first end 15 of the handle, there are disposed spaced-apart arms 19, 21. Each arm has a first portion 23, 25 extending laterally from the handle in a first direction, and second portions 27, 29 extending from the first portions in a second direction. As shown, the second portions are at right angles with respect to the first portions, so that the two arms 19, 21 are generally L-shaped, as viewed in a plane perpendicular to the axis 13 of handle 11. The second portions are slotted at the ends thereof for receiving a length of dental floss. The dental floss is inserted in the slots and tensioned between the two arms 19, 21. As shown, the dental floss is aligned parallel to the axis 13 of handle 11.

The second end 17 of the tool is configured with a compressible spring-type pin 31 designed for insertion into the socket of an actuating mechanism described hereinafter. Compressible pin 31 serves to secure the tool to the actuating mechanism. Pin 31 may be formed as an integral part of the handle 11 or attached thereto.

Preferably, the tool, including handle 11 and arms 19, 21, is formed as an integral unit. The tool may be molded as one piece from plastic, for example.

As an article of manufacture, the tool may be provided with dental floss 30 secured at the ends of arms 27, 29 and pre-tensioned for use. With this arrangement, the tool may be disposable, thus obviating the need for the user to remove one piece of dental floss and install a new one in its place.

The tool of FIG. 1a is particularly suited for flossing the left mandibular and right maxillary teeth in the jaw, as described hereinafter. FIG. 1b illustrates another version of the tool which is identical to the tool of FIG. 1a except that it is the mirror image thereof. The tool of FIG. 1b is particularly suited for flossing the right mandibular and left maxillary teeth.

FIG. 2 is a plan view of the teeth of one jaw which illustrates the use of the mirror-image versions of the dental flossing tool. Assume, for example, that the teeth are those in the mandible and that the tools are illustrated such that the second portions of the L-shaped arms extend into the plane of the paper. It can be seen from FIG. 2 that tool 33 corresponds to that shown in FIG. 1a; whereas tool 35 corresponds to that shown in FIG. 1b. Tool 33 is used to floss the left portion of the mandible, while the mirror-image tool 35 is used to floss the right portion of the mandible. When tool 33 is rotated 180° about the longitudinal axis of the handle, it is used to floss the right portion of the maxillary teeth. Similarly, tool 35 may be rotated 180° on its axis and used to floss the left portion of the maxillary teeth. It can be seen from FIG. 2 that both tools 33 and 35 are particularly advantageous for reaching the second bicuspids and rear molars, thereby reducing the effort required by the user in inserting the dental floss between the teeth in these target areas. Manual manipulation of the tools has been found to be similar to the user's natural action in brushing the teeth, thereby easing the flossing process. Because of the design of the tool, there is little distortion of the mouth or gouging of the internal surfaces of the cheek by the tool in use. In addition, the user may easily view the flossing activity in the target area with little interference or obstruction from the tool. Furthermore, the force applied by the user in flossing the rear teeth is in proper direction for satisfactorily scraping the surfaces between the teeth, both above and below the gum line.

FIG. 3 illustrates one version of the flossing tool mounted on an electrical actuating mechanism 37. Preferably device 37 includes a battery-powered electric motor mechaically linked to the flossing tool for reciprocally actuating the dental floss tensioned between the arms thereof. Device 37 may be the power unit of an electric toothbrush, for example. The flossing tool is detachably secured on actuating device 37 by inserting the compressible pin 31 (FIG. 1a) into a mating socket 38 illustrated in dashed outline form in FIG. 3. The pin and socket are dimensioned to provide a friction fit. Thus, the mirror-image versions of the flossing tool may be easily interchanged in the actuating device 37 for flossing different areas of the mouth. Also, the detachable pin and socket means for securing the tool to the actuating device provides a convenient arrangement for disposing of one tool when the dental floss is worn, and replacing the tool with a new one having a new length of pre-tensioned dental floss between the arms of the tool.

The reciprocal motion of the dental floss mounted on the tool may follow an arcuate path as illustrated by the direction arrows 39. Alternatively, the reciprocal motion may be linear as illustrated by arrows 41. The particular type of reciprocal motion achieved depends on the manner in which the motor of device 37 drives the handle of the flossing tool.

FIGS. 4a, b and c illustrate another embodiment of the dental flossing tool which may be configured in mirror-image versions. As shown in FIG. 4a, two L-shaped arms 43, 45 are secured to opposite ends of an intermediate support member 47. The ends of arms 43, 45 are slotted to hold a length of dental floss 49 therebetween, in the same manner as described above with respect to FIG. 1a. One end of the support member 47 is configured to define a receptacle 51, while the other end of support member 47 is configured to define another receptacle 52, as shown in FIG. 4. A handle 53 is provided with a pin-like portion 55 at one end thereof for insertion into either receptacle 51 or 52, so that the longitudinal axis of handle 53 and that of support member 47 are aligned. Pin 55 and receptacles 51, 52 are dimensioned for frictional engagement thereby to permit simple attachment and detachment of handle 53 to either end of support member 47. It can be seen that when handle 53 is attached in receptacle 52 of support member 47, the resulting assembly is similar to that shown in FIG. 1a; whereas the mirror-image assembly of FIG. 1b is produced by inserting handle 53 in receptacle 51 of support member 47. Thus, only one flossing tool assembly is necessary to floss all areas of the mouth.

The support member 47 and associated L-shaped arms 43, 45 may be formed as an integral unit from plastic and the dental floss 49 may be pre-tensioned between the two arms. When the dental floss has become worn, the unit of FIG. 4a may be discarded and replaced with a new unit containing a new length of pre-tensioned dental floss.

What is claimed is:

1. A dental flossing tool comprising:
   a handle having a longitudinal axis and first and second ends; and
   a pair of spaced-apart arms disposed on said handle at said first end thereof,
   said arms each having a first portion extending laterally from said handle in a first direction and a second portion extending from said first portion in a second direction, said first and second portions forming substantially an L-shaped geometry;
   the second portions of said arms being disposed for holding a length of dental floss between said arms in parallel alignment to the axis of said handle.

2. The tool of claim 1 wherein the second portions of said arms extend at right angles from the respective first portions of said arms.

3. The tool of claim 2, further including means disposed on the second portions of said arms for securing dental floss to said arms.

4. The tool of claim 3, further including dental floss tensioned between said securing means.

5. The tool of claim 1, wherein the first portions of said arms extend at right angles from said handle and the second portions of said arms extend at right angles from the respective first portions of said arms.

6. The tool of claim 1 further including means secured to the second end of said handle for reciprocally actuating the second portions of said arms that hold a length of dental floss.

7. The tool of claim 6, wherein said actuating means includes a hand-held housing containing an electric motor.

8. The tool of claim 6 wherein the second end of said handle and said actuating means are configured with mating friction-fit securing means, thereby to permit attachment and detachment of said handle from said actuating means.

9. A dental flossing tool comprising:
   a handle;
   a support member having first and second ends;
   first and second L-shaped arms disposed on said support member at said first and second ends, respectively, said arms having end portions configured to hold a length of dental floss therebetween;

said support member being configured at each of the first and second ends thereof for detachably securing said handle thereto;

said tool having first and second different mirror-image configurations when said handle is secured to said first and second ends, respectively, of said support member.

10. The tool of claim 9, wherein said support member includes a receptacle at each of the first and second ends thereof, and said handle includes a mating pin for frictional engagement in either receptacle.

11. The tool of claim 9 further including a length of dental floss tensioned between said arms.

* * * * *